United States Patent [19]

Imran et al.

[11] Patent Number: 5,666,968
[45] Date of Patent: Sep. 16, 1997

[54] FLEXIBLE GUIDE WIRE WITH EXTENSION CAPABILITY AND GUIDE WIRE EXTENSION FOR USE THEREWITH

[75] Inventors: Mir A. Imran, Palo Alto; Dennis L. Brooks, Santa Clara; Deepak R. Gandhi, San Jose, all of Calif.

[73] Assignee: Intelliwire, Inc., Sunnyvale, Calif.

[21] Appl. No.: 405,882

[22] Filed: Mar. 17, 1995

[51] Int. Cl.⁶ .................................................. A61B 5/00
[52] U.S. Cl. ............................................ 128/772; 118/657
[58] Field of Search ...................................... 128/657, 658, 128/772; 604/95, 280, 281, 282, 283

[56] References Cited

U.S. PATENT DOCUMENTS

| | | | |
|---|---|---|---|
| 5,238,005 | 8/1993 | Imran | 128/772 |
| 5,247,942 | 9/1993 | Prather et al. | 128/772 |
| 5,349,964 | 9/1994 | Imran | 128/772 |
| 5,357,979 | 10/1994 | Imran | 128/772 |
| 5,379,772 | 1/1995 | Imran | 128/662 |
| 5,415,178 | 5/1995 | Hsi et al. | 128/772 |

*Primary Examiner*—Max Hindenburg
*Assistant Examiner*—Pamela L. Wingood
*Attorney, Agent, or Firm*—Flehr, Hohbach, Test, Albritton & Herbert

[57] ABSTRACT

A guide wire with extension capability for use in a medical procedure having a guide wire and a guide wire extension. The guide wire comprises a flexible elongate cylindrical member having proximal and distal extremities. A portion of the distal extremity is formed of a material having high torquability and high pushability. The guide wire extension comprises a flexible elongate cylindrical member formed of a shape memory material. A major portion of the flexible elongate cylindrical member of the guide wire extension has a shape memory in the form of a coil so that when it is free it will assume a shape memory coil. A junction is formed between the proximal extremity of the guide wire and the distal extremity of the guide wire extension for connection of the guide wire extension to the guide wire.

11 Claims, 1 Drawing Sheet

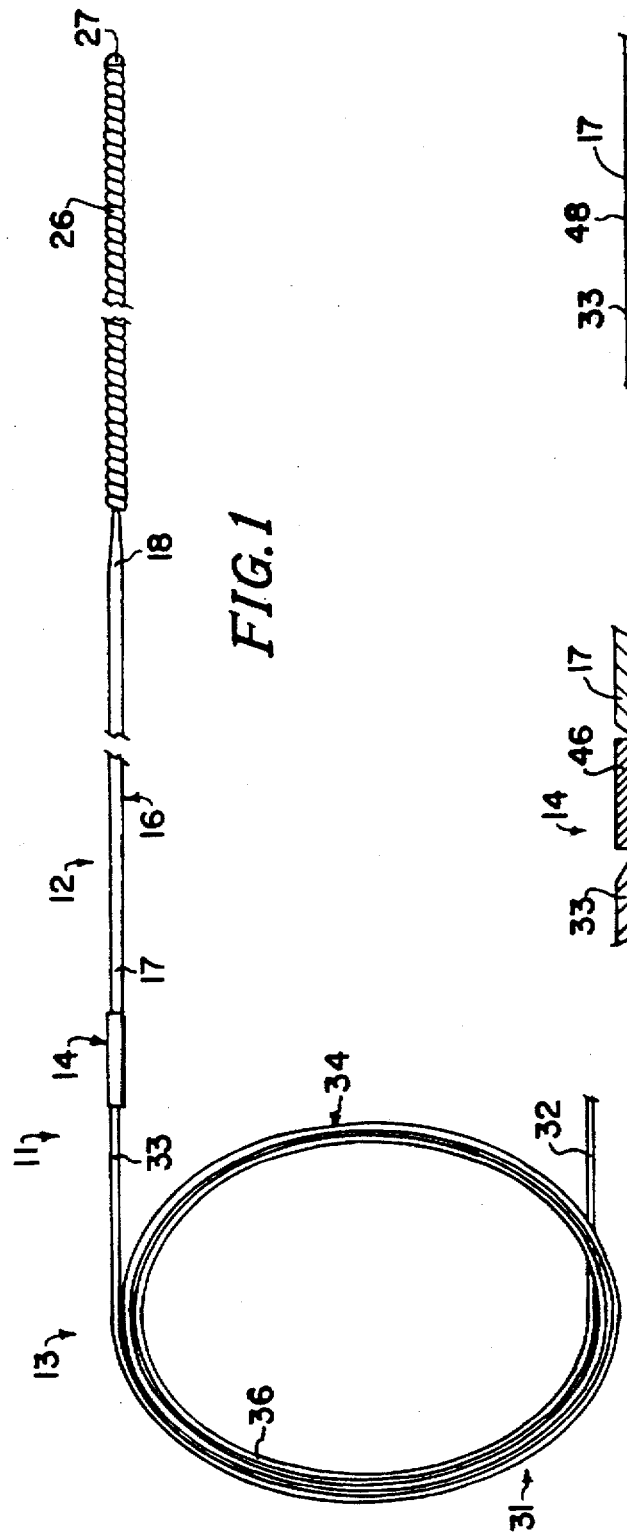

5,666,968

FLEXIBLE GUIDE WIRE WITH EXTENSION CAPABILITY AND GUIDE WIRE EXTENSION FOR USE THEREWITH

This invention relates to a flexible guide wire with extension capability, and more particularly to such guide wires which are to be used with over-the-wire catheters and particularly over-the-wire balloon catheters used in angioplasty and other procedures and to a guide wire extension for use therewith.

In the past, guide wires utilized in connection with over-the-wire catheters have typically had lengths ranging from 150 to 175 centimeters, although guide wires having lengths ranging up to 300 centimeters have been provided to facilitate the exchange of over-the-wire catheters, the use of such long guide wires has been found to be undesirable. Since they are so long it is necessary to hold and protect the long lengths of extension wires in order that it does not come into contact with anything that is non-sterile. For this reason, separate extension guide wires have been provided which have the capability of being detachably mounted on the proximal extremity of the guide wires. However, these are also disadvantageous because it is necessary to support such extension guide wires in a manner so that they do not touch anything which is non-sterile. Also, in order to avoid the use of extension wires, over-the-wire catheters have been provided which have rapid exchange capabilities eliminating the need for such extension wires. There is still need for a new and improved flexible guide wire which has an extension capability which overcomes the above disadvantages.

In general, it is an object of the present invention to provide a flexible guide wire with an extension capability which includes a guide wire extension having a recoil capability so that when it is free it forms a relatively compact coil that can readily be retained in a sterile environment.

Another object of the invention is to provide a flexible guide wire with an extension capability of the above character in which a guide wire extension can be permanently or detachably mounted on the proximal extremity of the guide wire.

Another object of the invention is to provide a flexible guide wire with extension capability of the above character which can be used by a single person in making an exchange of over-the-wire balloon catheters.

Another object of the invention is to provide a flexible guide wire with extension capability of the above character in which the guide wire extension can be utilized with a conventional guide wire having electrical capabilities.

Another object of the invention is to provide a flexible guide wire with extension capability of the above character in which the guide wire extension has a major portion that is provided with a coil shape memory.

Another object of the invention is to provide a flexible guide wire with extension capability of the above character in which the proximal and distal extremities of the guide wire extension have a straight shape memory.

Another object of the invention is to provide a flexible guide wire with extension capability of the above character which retains its desired torquability and pushability.

Another object of the invention is to provide a flexible guide wire with extension capability of the above character which can be economically manufactured.

Additional objects and features of the invention will appear from the following description in which the preferred embodiments are set forth in detail in conjunction with the accompanying drawings.

FIG. 1 is a side elevational view of a flexible guide wire with extension capability incorporating the present invention and including a guide wire and a guide wire extension in which the guide wire extension has a shape memory coil in which the coil has turns which lie in planes parallel to the longitudinal axis of the guide wire.

FIG. 2 is an enlarged side elevational view in section of the junction between the proximal extremity of the guide wire and the distal extremity of the guide wire extension which provides for detachable mounting.

FIG. 3 is a side elevational view in section of another embodiment of the junction shown in FIG. 2 and showing a permanent connection.

FIG. 4 is a side elevational view of another embodiment of the guide wire extension shown in FIG. 1 in which the turns of the coil lie in planes substantially perpendicular to the longitudinal axis of the guide wire.

In general, the flexible guide wire with extension capability for use in a medical procedure and comprised of a guide wire and a guide wire extension. The guide wire is comprised of a flexible elongate member having proximal and distal extremities and having a longitudinal axis. The flexible elongate member is formed of a material having high torquability and high pushability. The guide wire extension comprises a flexible elongate element having proximal and distal extremities and a longitudinal axis. At least a major portion of the guide wire extension is formed of a shape-memory material. The shape-memory material has a shape memory therein causing said major portion of the guide wire extension to form into a coil when it is free. The coil is adapted to be straightened out when the extension guide wire is in use. A connection is formed between the guide wire extension and the proximal extremity of the guide wire which may be permanent or detachable.

More particularly as shown in FIGS. 1 and 2 of the drawings, the guide wire with extension capabilities 11 incorporating the present invention is comprised of a guide wire 12 and a guide wire extension 13 and junction forming means 14 interconnecting the guide wire 12 and the guide wire extension 13.

The guide wire 12 can be constructed in a conventional manner such as those used in angioplasty procedures. Such guide wires typically can have a length of approximately 175 centimeters and a diameter of 0.014" or 0.018". Guide wires, however, can have sizes ranging from 0.010" to 0.032" and even larger in medical applications other than in angioplasty.

The guide wire 12 can be of a conventional construction. It is in the form of a flexible elongate cylindrical member 16 having proximal and distal extremities 17 and 18. Typically this flexible elongate cylindrical member 16 can be solid and be formed of a suitable material such as stainless steel having a suitable outside diameter, as for example 0.014" or 0.018". Alternatively, the elongate cylindrical member can be in the form of a stainless steel tubular member typically called a hypotube. It can have a wall thickness of 0.002" to 0.003" inches to provide a lumen (not shown) and have a suitable size, as for example 0.012" through which a core wire or mandrel (not shown) of a suitable diameter as for example 0.010" extends from the proximal extremity 17 to the distal extremity 18 of the flexible elongate cylindrical member 16. The distal extremity of the flexible elongate cylindrical member 16 or the core wire (not shown) as is well known to those skilled in the art can be provided with portions of reduced diameter to provide additional flexibility for the distal extremity of the guide wire 12.

A flexible coil spring 26 is mounted on the distal extremity of the flexible elongate cylindrical member 16 by suitable means such as an adhesive. A rounded tip 27 formed of a suitable material such as solder is provided on the distal extremity of the spring 26. The spring 26 can have any suitable length as for example a length of 30 centimeters for a guide wire 12 having a total length of 175 centimeters. As explained previously, this guide wire 12 is of a conventional construction and therefore further details of its construction are not given.

The guide wire extension 13 of the present invention consists of a flexible elongate cylindrical member 31 having proximal and distal extremities 32 and 33. The flexible elongate cylindrical member 31 can have a suitable length as for example 150 centimeters generally corresponding to the length of the guide wire 12 so that the total combined length is at least about 300 centimeters. In accordance with the present invention, the flexible elongate cylindrical member 31 of the guide wire extension 13 is formed of a shape memory material as for example a nickel titanium alloy. The flexible elongate cylindrical member 31 is solid and can have a slightly smaller diameter than the guide wire. Thus for example with a guide wire 12 having a diameter of 0.014" to 0.018", the flexible elongate cylindrical member 31 can have an outside diameter ranging from 0.012" to 0.014". In accordance with the present invention, the proximal extremity 32 and the distal extremity 33 are provided with a straight shape memory as is shown in FIG. 1, whereas the major portion of the flexible elongate cylindrical member 31 intermediate the proximal and distal extremities 32 and 33 has a coil shape having a diameter ranging from 2.0" to 8.0", so that when the flexible elongate tubular member 31 is free, it will recoil itself into a coil 34 shown in FIG. 1. As shown, the coil 34 is provided with a plurality of turns 36 with the number of turns being increased with a decreased size for the diameter of the coil and decreased with an increased size in the diameter of the coil. The coil 34 which is formed lies in a plane generally parallel to the longitudinal axis of the guide wire 12.

Connection means is provided for forming the connection or junction 14 between the distal extremity 33 of the guide wire extension 13 and the proximal extremity 17 of the guide wire 12. As shown particularly in FIGS. 1 and 2, this means consists of a sleeve 46 formed of a suitable material such as stainless steel which has one end of the same crimped onto a plunge ground portion 33a of the distal extremity 33 of the guide wire extension 13. Alternatively, an adhesive or solder can be used to fasten the sleeve 46 to the distal extremity 33. Typically the sleeve 46 should not have an outer diameter which is much greater than the outer diameter of the guide wire 12. Typically the distal extremity of the guide wire extension 13 will only extend partially into the sleeve 46 so that the plunge ground portion 17a of the proximal extremity 17 of the flexible elongate cylindrical member 16 can fit within the other end of the sleeve 46 and be detachably retained therein by cooperative releasable means such as by a friction fit or a thermoplastic adhesive.

Alternatively, as shown in FIG. 3, the junction 14 can be in the form of a junction 41 which can be in the form of a solder joint or weld which permanently joins the two portions in a butt joint and provides a smooth transition from the guide wire 12 to the guide wire extension 13.

Another embodiment of the guide wire extension 51 incorporating the present invention is shown in FIG. 4. It consists of a flexible elongate cylindrical member 52 having proximal and distal extremities 53 and 54. As with the guide wire extension 13, the flexible elongate cylindrical member 52 is formed of a shape memory material having the same length and diameter. As shown in FIG. 4, the proximal and distal extremities 53 and 54 are given a straight shape memory whereas the major portion intermediate the same is formed into a coil 56 having a plurality of turns 57. Typically the coil 56 would be of a smaller diameter than the coil 34, because as shown in FIG. 4 the coil is designed so that its axis is parallel to that longitudinal axis of the guide wire extension 51 and the individual turns of the coil lie in planes which are substantially perpendicular to the longitudinal axis. Typically the turns 57 of the coil 56 would be of a smaller diameter than the turns 36 of the coil 34 so that the turns will remain substantially vertical when the coil 56 is lying on a surface. The guide wire extension can be secured to a guide wire 12 in the same manner as the guide wire extension 13. Thus, by way of example, a sleeve 61 has been provided on the straight shape memory distal extremity 54 and is affixed thereto in the manner described for the sleeve 46. The sleeve 61 is adapted to be removably attached to the guide wire 12 also in the manner described for the sleeve 46.

Operation and use of the guide wire with extension capabilities 11 may now be briefly described in conjunction with a conventional angioplasty procedure. Let it be assumed that the guide wire 11 has been positioned in a coronary vessel. While this was taking place, the coil 36 can be resting on the operating table on the drapes over the patient so that it remains in a sterile field with it being unnecessary for nurse or other attendant to hold the same while the guide wire is being advanced into the coronary vessel. Thus, the physician can perform this procedure by himself. If the guide wire extension 13 is permanently attached to the guide wire 11, the guide wire extension 13 can be stretched out against the force of the shape memory material and the over-the-wire balloon catheter threaded over the extension guide wire and then over the guide wire into the coronary vessel of the patient until the balloon carried by the catheter is disposed in the stenosis on which it is desired to perform an angioplasty procedure. Thereafter in a manner well known to those skilled in the art the balloon of the catheter can be inflated to attempt to increase the flow passage through the stenosis. Let it be assumed that it is desired to thereafter utilize another angioplasty catheter having larger balloon thereon. Keeping the guide wire 11 in place, the first angioplasty catheter is withdrawn over the guide wire 12 and over the guide wire extension 13 by uncoiling the guide wire extension 13. Thereafter another over-the-wire balloon catheter having a balloon thereon is threaded onto the guide wire extension 13 as it is uncoiled and then advanced into the vessel of the patient over the guide wire 12, which still remains in position in the stenosis and into the stenosis. Thereafter, the larger balloon carried by the over-the-wire balloon catheter can be inflated to still further increase the blood flow passage through the stenosis. Thereafter, the over-the-wire balloon catheter can be removed in the same manner as the first over-the-wire balloon catheter followed by the removal of the guide wire 11 as well as the guiding catheter which is typically used. Thereafter the cut formed in the femoral artery can be sutured in a conventional manner to complete the procedure.

In the event it is desired to utilize a guide wire with extension capabilities 11 having a detachable guide wire extension, the detachable connecting means shown in FIG. 2 utilized to secure the guide wire extension 13 to the guide wire 12 after which the guide wire 11 can be advanced in the patient in the vessel of the patient in the manner hereinbefore described and used as hereinbefore described.

The embodiment of the guide wire extension 51 shown in FIG. 4 can also be utilized in the same manner as the guide wire extension 13 shown in FIG. 1 with the coils in both embodiments being readily extendable so that an over-the wire balloon catheter can be passed over the same. Guide wire extensions 13 and 51 are formed in such a manner so that they take very little space in their coiled form and can be readily placed in a sterile field near the patient so that they need not be held by an attendant during the procedure making it possible for a single person to perform the procedure. The coils have sufficient strength in their memory so that they will return or recoil to the recoiled positions as shown in FIGS. 1 and 4 when they are free and lying on a generally planar surface. This is particularly advantageous in that there is not an unnecessary length of wire which the physician performing the procedure needs to keep out of the way and keep in a sterile field.

With such a guide wire with extension capabilities, a conventional guide wire having good torquability and pushability can be retained while still providing a guide wire extension which has the unique capabilities of the present invention of having a shape memory which causes it to return or recoil into a coiled configuration that requires little space and which can lie on a relatively planar surface in a sterile field adjacent the patient so that it is ready for use.

As disclosed previously, the guide wire with extension capabilities can have the guide wire extension permanently attached so that it can be sterilized by the manufacturer and be ready to use. The coil which is formed in the guide wire extension will not affect the torquability of the guide wire, nor will it affect the conventional characteristics of the guide wire 12. All that is done is that the extension guide wire has been provided with a shape set to prevent it from falling off the operating table and touching non-sterile surroundings. By having the guide wire with extension capabilities utilizing a conventional guide wire, the pushability and torquability as well as trackability of existing guide wires can be retained while still obtaining the advantages of the guide wire extension utilized disclosed herein.

Although the guide wire with extension capabilities 11 has been disclosed as being provided without electrical capabilities, it should be appreciated that the same concepts can be utilized with guide wires having electrical capabilities. For example, as disclosed in U.S. Pat. No. 5,238,005, steering of the distal extremity of the guide wire can be provided. A guide wire having such capabilities in place can have the electrical connections removed and a guide wire extension 13 of the type hereinbefore described connected to the same and utilized for exchanging over-the-wire balloon catheters in the manner hereinbefore described. Similarly, other electrical guide wires can be provided such as those disclosed in U.S. Pat. No. 5,349,964 having a current shunt, electrical guide wires such as disclosed in U.S. Pat. No. 5,357,979 having current controlled adjustable stiffness and adjustable bend locations, and electrical guide wires such as disclosed in U.S. Pat. No. 5,379,772 having forward-looking ultrasonic imaging capabilities. All of the guide wires of this type can utilize a guide wire extension incorporating the present invention.

The guide wire extension of the present invention is also advantageous in that it is relatively simple in construction and can be readily and economically manufactured.

What is claimed:

1. A guide wire assembly with extension capability for use in a medical procedure in a body comprising a guide wire and guide wire extension, said guide wire comprising a flexible elongate member having proximal and distal extremities and a longitudinal axis, at least a portion of the distal extremity being formed of a material having high torquability and high pushability, said guide wire extension comprising a flexible elongate member formed of a shape memory material and having a major portion thereof having a shape memory in the form of a coil so that when it is outside the body will assume its shape of a shape memory coil and means for forming a junction between the proximal extremity of the guide wire and the distal extremity of the guide wire extension.

2. A guide wire assembly as in claim 1 wherein the proximal and distal extremities of the guide wire extension are provided with a straight memory.

3. A guide wire assembly as in claim 1 wherein the coil has turns which lie in a plane which are parallel to the longitudinal axis of the guide wire.

4. A guide wire assembly as in claim 1 wherein the turns of the coil lie in planes which are generally perpendicular to the longitudinal axis of the guide wire.

5. A guide wire assembly as in claim 1 wherein said means forming a junction is in the form of means forming a permanent connection between the guide wire and the guide wire extension.

6. A guide wire assembly as in claim 1 wherein said means forming a junction is comprised of a sleeve and wherein the distal extremity of the guide wire extension and the proximal extremity of the guide wire are disposed in the sleeve and cooperative releasable means carried by the sleeve engaging the proximal extremity of the guide wire for removably retaining the guide wire within the sleeve.

7. A guide wire assembly as in claim 6 wherein said sleeve is affixed to said guide wire extension.

8. A guide wire extension for use with a guide wire having proximal and distal extremities comprising a flexible elongate member having proximal and distal extremities, said flexible elongate member being formed of a shape memory material and having a major portion thereof having a shape memory in the form of a coil so that when the extension guide wire is free, said major portion will assume the shape of a shape memory coil.

9. A guide wire extension as in claim 8 wherein the proximal and distal extremities of the flexible elongate member are provided with a straight memory.

10. A guide wire extension as in claim 8 wherein said coil has turns which lie in planes that are parallel to the longitudinal axis of the guide wire extension.

11. A guide wire extension as in claim 8 wherein said coil has turns which lie in planes that are generally perpendicular to the longitudinal axis of the guide wire extension.

* * * * *